US009468380B2

(12) United States Patent
Hirsch et al.

(10) Patent No.: US 9,468,380 B2
(45) Date of Patent: Oct. 18, 2016

(54) METHOD TO IDENTIFY TISSUE OXYGENATION STATE BY SPECTROGRAPHIC ANALYSIS

(71) Applicant: Children's Hospital Medical Center, Cincinnati, OH (US)

(72) Inventors: Russel Hirsch, Cincinnati, OH (US); John Miras Racadio, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 309 days.

(21) Appl. No.: 13/854,571

(22) Filed: Apr. 1, 2013

(65) Prior Publication Data

US 2013/0295192 A1    Nov. 7, 2013

Related U.S. Application Data

(60) Provisional application No. 61/618,285, filed on Mar. 30, 2012.

(51) Int. Cl.
*A61B 5/1459* (2006.01)
*A61B 5/00* (2006.01)
*A61B 5/1455* (2006.01)
*A61B 18/24* (2006.01)

(52) U.S. Cl.
CPC ......... *A61B 5/0075* (2013.01); *A61B 5/14551* (2013.01); *A61B 5/6848* (2013.01); *A61B 18/24* (2013.01)

(58) Field of Classification Search
None
See application file for complete search history.

(56) References Cited

U.S. PATENT DOCUMENTS

| | | | | |
|---|---|---|---|---|
| 5,329,922 | A * | 7/1994 | Atlee, III | 600/328 |
| 5,435,308 | A * | 7/1995 | Gallup et al. | 600/342 |
| 5,611,338 | A * | 3/1997 | Gallup et al. | 600/342 |
| 6,498,652 | B1 * | 12/2002 | Varshneya et al. | 356/477 |
| 6,564,087 | B1 | 5/2003 | Pitris et al. | |
| 6,564,088 | B1 * | 5/2003 | Soller et al. | 600/478 |
| 6,816,266 | B2 * | 11/2004 | Varshneya et al. | 356/477 |
| 8,812,080 | B2 * | 8/2014 | Nachabe et al. | 600/424 |
| 2005/0154277 | A1 | 7/2005 | Tang et al. | |
| 2008/0125634 | A1 * | 5/2008 | Ryan et al. | 600/342 |
| 2010/0210931 | A1 | 8/2010 | Cuccia et al. | |
| 2010/0278738 | A1 | 11/2010 | Sitzman et al. | |
| 2010/0317964 | A1 | 12/2010 | Hendriks et al. | |
| 2010/0331782 | A1 | 12/2010 | Hendriks et al. | |

FOREIGN PATENT DOCUMENTS

| | | | |
|---|---|---|---|
| WO | WO 03/020119 | 3/2003 | |
| WO | WO 2007/083310 | 7/2007 | |
| WO | WO 2007147058 A2 * | 12/2007 | |
| WO | WO 2009/050667 | 4/2009 | |
| WO | WO 2009/109879 | 9/2009 | |
| WO | WO 2010143119 A2 * | 12/2010 | |
| WO | WO 2011066429 A1 * | 6/2011 | ......... A61B 5/14551 |

OTHER PUBLICATIONS

Donnelly, Andrew J and Djuric, Michael "Cardioplegia solutions" Am J Hosp Pharm. Nov. 1991;48(11):2444-60.*
Prahl, Scott "Optical Absorption of Hemoglobin" Oregon Medical Laser Center (OMLC), Dec. 15, 1999, 3 pages.*
Prahl, Scott "Tabulated Molar Extinction Coefficient for Hemoglobin in Water" Oregon Medical Laser Center (OMLC), Mar. 4, 1998, 7 pages.*
Knobloch, Karsten "The role of tendon microcirculation in Achilles and patellar tendinopathy" Journal of Orthopaedic Surgery and Research, Apr. 30, 2008, 3(18), 13 pages, doi:10.1186/1749-799X-3-18.*
Arifer et al., Spatially resolved reflectance spectroscopy for diagnosis of cervical precancer; Monte Carlo modeling and comparison to clinical measurements, Journal of Biomedical Optics 11(6), 064027 (Nov./Dec. 2006).
Nachabe et al., Estimation of lipid and water concentrations in scattering media with diffuse optical spectroscopy from 900 to 1600 nm, Journal of Biomedical Optics 15(3), 037015 (May/Jun. 2010).
Desjardins et al., Needle stylet with integrated optical fibers for spectroscopic contrast during peripheral nerve blocks, Journal of Biomedical Optics 16(7), 077004 (Jul. 2011).

* cited by examiner

*Primary Examiner* — Louise W Humphrey
*Assistant Examiner* — Aaron J Kosar
(74) *Attorney, Agent, or Firm* — Faegre Baker Daniels LLP

(57) ABSTRACT

A system and method for identifying metabolic activity within the heart muscle (myocardium). Metabolic activity is determined through spectrographic analysis of the myocardium. More particularly, oxygen saturation of the myocardium is measured through the spectrographic analysis, and metabolic activity is measured by a decrease in oxygen saturation of the myocardium over time.

18 Claims, 2 Drawing Sheets

METHOD TO IDENTIFY TISSUE OXYGENATION STATE BY SPECTROGRAPHIC ANALYSIS

CROSS-REFERENCE TO RELATED APPLICATION

This application claims the benefit of U.S. Provisional Application No. 61/618,285, filed Mar. 30, 2012, the disclosures of which are expressly incorporated by reference herein.

BACKGROUND AND SUMMARY OF THE DISCLOSURE

The present disclosure relates to identifying aerobic activity within the heart muscle (myocardium) and, more particularly, to measuring changes in intra-myocardial oxygen saturation during cardiac surgery.

During heart surgery, patients placed on cardiopulmonary bypass typically undergo myocardial protection through the administration of cardioplegia solution and myocardial cooling. Such a procedure reduces or arrests aerobic and metabolic activity, including contractions, within the myocardium (protected cardiac arrest). Metabolic arrest avoids ischemic damage, prevents the accumulation of toxic metabolites and aims to alleviate post-operative inflammation and dysfunction. While there is a general presumption that intra-myocardial metabolic and aerobic activity is largely arrested during protected cardiac arrest, there is currently no practical and sensitive manner to determine this.

As a result, repeat administration of cardioplegia solution for ongoing myocardial protection is empiric at best, and often only when spontaneous myocardial electrical activity is appreciated. This lack of insight into the metabolic and aerobic activity may result in inadequate myocardial protection. A need thus exists for a method to effectively measure metabolic and aerobic activity within the myocardium during times of presumed adequate protection during a surgical intervention. The method described in this disclosure would improve the assessment of intra-myocardial metabolic and aerobic activity and would be vital to transforming the processes used to adequately protect the myocardium during such surgical procedures.

The present disclosure relates to the use of a conventional photonic needle in the myocardium to measure real time changes in myocardial tissue oxygen saturation. One such photonic needle is able to determine various tissue characteristics based on the absorption of a given spectrum of applied light, including the measurement of tissue oxygen saturation. The decrease in intra-myocardial oxygen saturation during protected cardiac arrest is indicative of low-grade, but ongoing aerobic processes (i.e. metabolic activity). With a better understanding of changes in myocardial oxygen saturation during protected cardiac arrest, alterations in cardioplegia administration strategies may be implemented to better protect the myocardium, increase the amount of time the surgeon has to perform the operation, improve subsequent cardiac function, and decrease recovery time after surgery.

According to an illustrative embodiment of the present disclosure, a method includes the steps of inserting a distal end of a photonic needle into myocardium, emitting light from the distal end of the photonic needle within the myocardium, and detecting light reflected from the myocardium. The method also includes the steps of processing the reflected light to determine intra-myocardial oxygen saturation. This will, in turn, provide the assessment of the baseline metabolic state of the myocardium.

According to an illustrative embodiment of the present disclosure, a method is provided for measuring oxygen saturation in the myocardium. The method includes the step of inserting a photonic needle within the myocardium, wherein the photonic needle includes a shaft, a first optic fiber extending within the shaft and coupled to a light source, and a second optic fiber extending within the shaft and coupled to a light detector. The method further includes the steps of emitting light from the first optic fiber, collecting light with the second optic fiber, obtaining spectroscopic data from light delivered and collected from the myocardium via the photonic needle, and processing the spectroscopic data to measure oxygen saturation in the myocardium. A further step will include detecting myocardial metabolic activity based upon changes in the measured oxygen saturation of the myocardium.

The illustrative method of the present disclosure utilizes the photonic needle to measure changes in myocardial tissue oxygen saturation levels during periods of protected cardiac arrest, where as previously defined, protected cardiac arrest is understood to be the cessation of cardiac contraction and electrical activity induced typically after aortic cross clamp, myocardial cooling, and cardioplegia administration. As such, there is a presumption that myocardial tissue oxygen saturation should remain constant (i.e. no utilization of oxygen), or decline very gradually over time. If the above presumption is not borne out (i.e. a rapid decline in myocardial oxygen saturation), this method would allow clinicians to monitor those changes in myocardial oxygen saturation in real-time, and alter myocardial protective strategies accordingly (as this would indicate ongoing metabolic activity in an ischemic environment that would result in more tissue damage). With improved understanding of the changes in myocardial oxygen saturation during protected cardiac arrest, alterations in cardioplegia composition and administration strategies may be used to better protect the myocardium, increase the amount of time that the surgeon has to perform the operation, improve subsequent cardiac function, and decrease recovery time after surgery.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1:
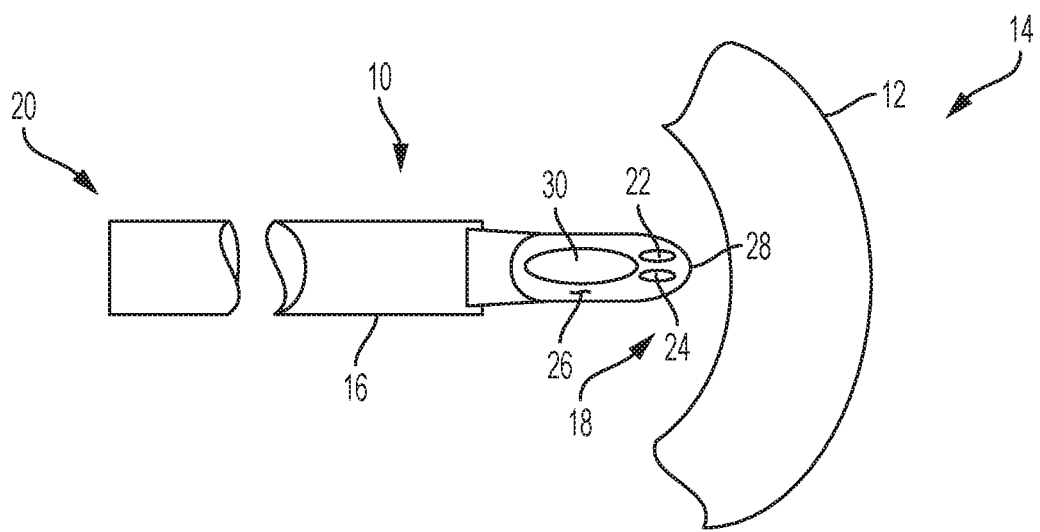
FIG. 1 is a diagrammatic view of the distal end of an illustrative photonic needle for use with a method of the present disclosure and positioned adjacent myocardial tissue.

Referring initially to FIG. 1, an illustrative photonic needle 10 is shown for use with the method of the present disclosure by detecting oxygenation state (i.e., oxygen saturation) of myocardium 12 of a heart 14. The photonic needle 10 may be of conventional design including a cylindrical shaft 16 having opposing distal and proximal ends 18 and 20. Light conduits, illustratively optic fibers 22 and 24, extend through the shaft 16. Optic fiber 22 is configured to deliver light to the myocardium 12, while optic fiber 24 is configured to collect reflected light from the myocardium 12.

Distal end 18 of the photonic needle 10 illustratively includes a beveled surface 26 defining an acute angle with the shaft 16 thereby defining a blade or pointed tip 28. (A channel 30 illustratively extends within the shaft 16 and may be used to extract substances from the myocardium 12 in which the needle 10 is positioned, or to deliver substances (e.g. contrast agents or drugs) to the myocardium 12). One such photonic needle 10 is offered by Philips Research and is able to determine various tissue characteristics based on the absorption of a given spectrum of applied light, including the measurement of tissue oxygen saturation. Additional details of illustrative photonic needles and operation thereof are provided in US Patent Application Publication No. 2010/0317964 to Hendriks et al., US Patent Application Publication No. 2010/0331782 to Hendriks et al., PCT International Patent Application Publication No. 2007/147058 to Ryan, and PCT International Patent Application Publication No. WO 2010/143119 to Nachabe et al., the disclosures of which are expressly incorporated by reference herein.

Figure 2:
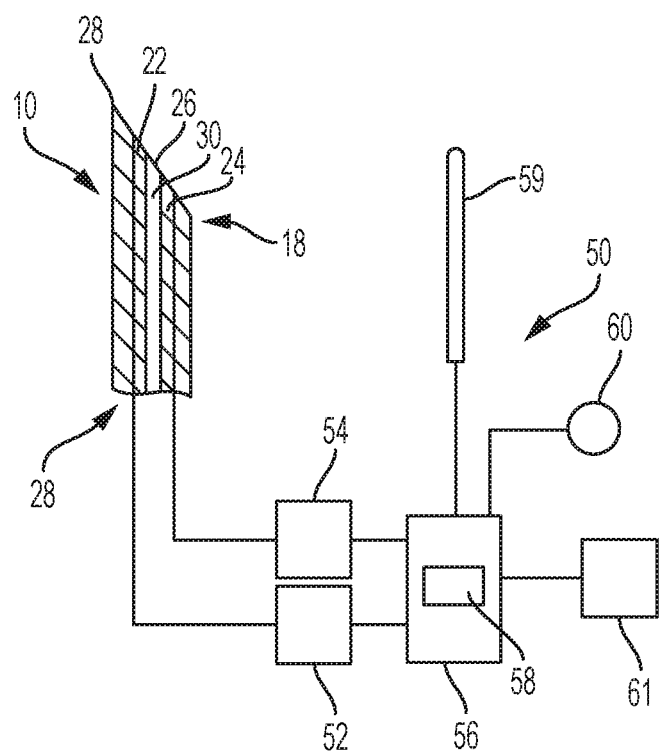
FIG. 2 is a schematic view of the illustrative photonic needle of FIG. 1 electrically coupled to a control system.

FIG. 2 shows an illustrative system 50 for processing and displaying a wavelength spectrum of the myocardium 12 adjacent the tip 28 of the photonic needle 10 based upon the reflected light collected at the distal end 18 by the optic fiber 24. Optic fiber 22 is shown operably coupled to an external light source 52, while optic fiber 24 is shown operably coupled to a light detector 54. A controller 56 is operably coupled to the light source 52 and light detector 54 and illustratively includes a processor 58. (A conventional myocardial temperature probe 59 may also be in communication with the controller 56 for measuring the temperature of the myocardium 12 and provide a signal indicative thereof to the processor 58). A user interface 61 is in communication with the controller 56 and is configured to receive input from, and provide output to, a user.

In operation, the controller 56 operates the light source 52 to emit light through the optic fiber 22 such that the light will be emitted at the distal end of the photonic needle 10 and into the surrounding myocardium 12. Part of the reflected and emitted light is collected by the light detector 54 through the optic fiber 24 proximate the distal end of the photonic needle 10. The light detector 54 transforms the detected light into electrical signals processed by the controller 56 for output to the user interface 61, illustratively a monitor. As further detailed herein, the reflected light spectrum provided by user interface 60 measures myocardial tissue oxygen saturation, thereby allowing the user to monitor metabolic activity within the myocardium 12. More particularly, a decrease in measured oxygen saturation of the myocardium 12 from a baseline value may provide an indication of myocardial metabolic activity.

Oxygen saturation of the myocardium 12 at the distal end 18 of the photonic needle 10 may be derived by the controller 60 computing the ratio of estimated oxygenated hemoglobin ($HbO_2$) concentration divided by the total hemoglobin (Hb) concentration (i.e. oxygenated and deoxygenated hemoglobin). Oxygenated and deoxygenated hemoglobin have very distinct light absorption properties yielding accurate saturation level estimations.

Figure 4:
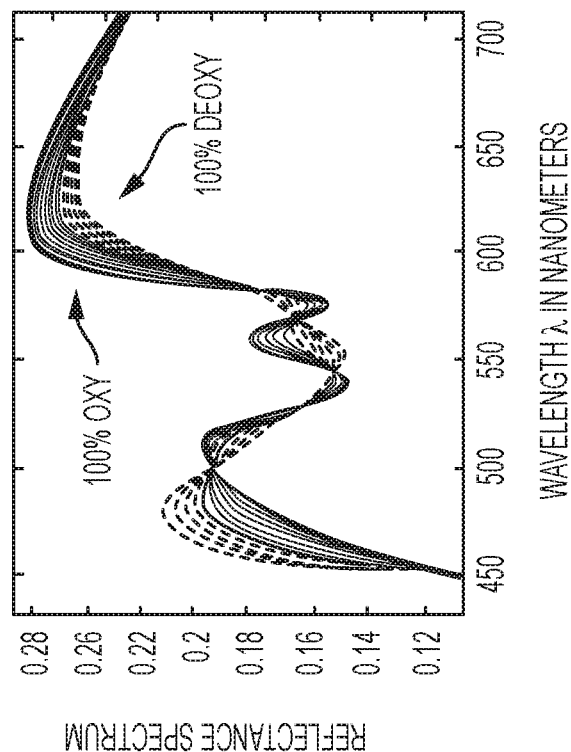
FIG. 4 is a chart of reflectance spectrum taken across a range of wavelengths comparing various oxygenated hemoglobin within tissue, such as myocardium.
Figure 3:
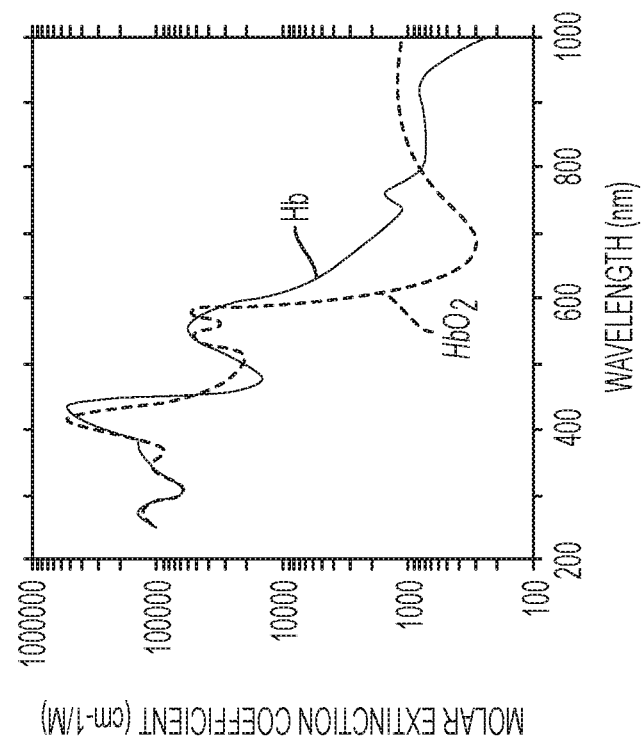
FIG. 3 is a chart of molar extinction coefficient taken across a range of wavelengths comparing oxygenated and deoxygenated hemoglobin within tissue, such as myocardium.

With reference to FIG. 3, molar extinction coefficients of oxygenated and deoxygenated hemoglobin ($HbO_2$ and Hb) within tissue, such as the myocardium 12, are shown across a range of wavelengths of light that may be emitted and received from photonic needle 10. As known, molar extinction coefficients are parameters defining how strongly a substance absorbs light at a given wavelength per molar concentration. FIG. 4 illustrates light reflective spectrums for hemoglobin (again within tissue, such as the myocardium 12) ranging from fully oxygenated and to deoxygenated across a range of wavelengths of light that may be emitted and received from photonic needle 10.

The following details proposed study protocols in support of the illustrative method detailed herein and in no way limit the scope of the invention.

Proposed Study Protocols

Hypothesis One: During periods of arrested cardiac activity (e.g., after cardio-pulmonary bypass institution, myocardial cooling, aortic cross-clamping and single dose cardioplegia solution administration) intra-myocardial oxygen saturation (as illustratively measured by the photonic needle 10) will decrease over time, possibly indicating ongoing aerobic metabolic activity (i.e. without ongoing myocardial protection, myocardial oxygen utilization will continue).

Hypothesis Two: Given stable conditions (e.g., stable cardio-pulmonary bypass and myocardial temperature), regularly repeated administration of cardioplegia solution, or a continuous infusion of cardioplegia will abolish the decrease in intra-myocardial oxygen saturation (i.e. improved myocardial protection will decrease myocardial oxygen utilization).

Hypothesis Three: During periods of arrested cardiac activity (e.g., after cardio-pulmonary bypass institution, aortic cross-clamping and single dose cardioplegia solution administration) intra-myocardial oxygen saturation will decrease at a faster rate at higher temperatures (i.e. increased oxygen utilization at higher temperatures).

The following illustrative study protocols will utilize a pig for the purpose of instituting cardio-pulmonary bypass, and each sub-protocol will be performed on two such animals.

Sub-Protocol A: Animal 1 and 2.
1. The animal will be placed under deep general anesthesia. Monitoring will include standard electrocardiogram (ECG) electrodes 60 and oxygen saturation monitor probes
2. When stable, and adequately monitored, a sternotomy will be performed and aortic and right atrial bypass cannulas will be inserted. The animal will be systemically heparinized (400 units/kg). The animal will then be ventilated with 100% oxygen for 5 minutes before proceeding.
3. Two photonic needles 10 will be positioned in stable positions within the heart 14, one within the myocardium 12 at the apex of the left ventricle, and the other within the myocardium 12 toward the right ventricle apex. Continuous saturation monitoring will then commence.

4. A myocardial temperature probe 59 will be positioned in a suitable location close to the photonic needles 10, but placed to avoid any interference with needle function.
5. Continuous oxygen saturation (from photonic needle 10), ECG (from electrodes 60) and temperature data (from probe 59) collection will then begin, and continue for the duration of the entire case.
6. Cardio-pulmonary bypass will commence at a volume of 80 ml/kg.
7. Cooling will commence until a core temperature of 28° C. has been reached. Experimental recording will begin at this time.
8. When stable data collection is established (parameters in table below), an aortic cross clamp will then be applied and cold (3-5° C.) cardioplegia solution infused once ante-grade into the aortic root (Cardioplegia Admin #1). The heart will be bathed in iced saline slush.
9. Myocardial temperature will be kept within 3° C. of the stable temperature achieved after repeated application of iced saline/saline slush.
10. Once cardiac arrest has been achieved, the open chest cavity will be covered with a dry sterile towel, and no further direct light will be applied to the site.
11. Data collection will occur according to Table 1.

(See Appendix 1a for constitution of cardio-pulmonary bypass prime fluid, and Appendix 1b for Cardioplegia solution constitution and administration rates for all aspects of the protocol.)

Assumption #A1:

Myocardial oxygen saturation will remain stable for a given period, and then begin to decrease over time, reflective of myocardial oxygen utilization/ongoing metabolic activity, as per Hypothesis One above.

Then the protocol will continue with animals 1 and 2 as follows:
1. When myocardial oxygen saturation has decreased by more than 15% from baseline, irrespective of the presence or absence of surface ECG activity, a repeat dose of cold (3-5° C.) cardioplegia solution will be infused into the aortic root, with re-establishment of a baseline myocardial saturation level (Cardioplegia Admin #2). The myocardium will continue to be intermittently bathed in iced saline slush to maintain the myocardial temperature within in at least 3° C. of the baseline temperature.
2. Data collection will continue as per the above table from the point of cardioplegia solution administration #2 for a period of 60 minutes.

Assumption #A2:

After the repeat cardioplegia solution infusion, myocardial oxygen saturation will remain stable (no further decrease), or will increase to a new level (close to the original baseline), and will then remain stable, (as per Hypothesis Two above) prior to declining (as per Hypothesis One above).

When the intra-myocardial oxygen saturation has decreased by 15%, the protocol will continue with animals 1 and 2 as follows:
1. Cardio-pulmonary bypass flow will be decreased by half, and the animal will be rewarmed to 35° C.
2. The aortic cross-clamp will then be removed, and myocardial perfusion will resume.
3. Once sinus rhythm has commenced, myocardial saturation data will continue to be collected as per Table 1 for a further period of 60 minutes.

Sub-Protocol B: Animal 3 and 4.

The protocol will follow that as outlined above for Sub-Protocol A up to step number 7 above. At that point, the protocol will differ in the following way:
1. When stable data collection is established (parameters in table below), the aortic cross clamp will then be applied and a continuous infusion of cold (3-5° C.) cardioplegia solution will be infused ante-grade into the aortic root, and maintained for the duration of the experiment.
2. Myocardial temperature will be kept within 3° C. of the lowest temperature measured with the repeated application of iced saline/saline slush.
3. Data collection will occur according to Table 2.

Assumption #B1:

Myocardial oxygen saturation will remain stable, or will decline at a slower rate compared with the decline as noted in Protocol A, indicative of arrested or slowed metabolic activity as per Hypothesis Two, above.

When the intra-myocardial saturation has decreased by 15%, the protocol will continue with animals 3 and 4 as follows:
1. Cardio-pulmonary bypass flow will be decreased by half, and the animal will be rewarmed to 35° C.
2. The aortic cross-clamp will then be removed, and myocardial perfusion will resume.
3. Once sinus rhythm has commenced, myocardial saturation data will continue to be collected as per Table 2 for a further period of 60 minutes.

Sub-Protocol C: Animal 5 and 6.

The protocol will follow that as outlined above for Sub-Protocol A and B, up to step number 7 above. At that point, the protocol will differ in the following way:
1. When stable data collection is established (parameters in table below), the aortic cross clamp will then be applied and room-temperature cardioplegia solution will be infused once ante-grade into the aortic root (Cardioplegia Admin #1). No topical iced slush will be applied to the myocardium.
2. Data collection will occur according to Table 1.

Assumption #C1:

Myocardial oxygen saturation will remain stable for a given period, and then begins to decrease over time, reflective of myocardial oxygen utilization/ongoing metabolic activity, as per Hypothesis One. The decline in oxygen saturation will be more rapid than that detected in Sub-Protocol A, indicative of greater metabolic activity and increased tissue oxygen utilization at higher myocardial temperature.

Then the protocol will continue with animals 5 and 6 as follows:
1. When myocardial saturation has decreased by more than 15% from baseline, irrespective of the presence or absence of surface ECG activity, a repeat dose of room-temperature cardioplegia solution will be infused into the aortic root, with re-establishment of a baseline myocardial saturation level (Cardioplegia Admin #2).
2. Data collection will continue as per the above table from the point of cardioplegia solution administration #2.
3. When intra-myocardial oxygen saturation has decreased by 15% from the initial baseline, cardio-pulmonary bypass flow will be decreased by half, and the animal will be rewarmed to 35° C.

4. The aortic cross-clamp will then be removed, and myocardial perfusion will resume.
5. Once sinus rhythm has commenced, myocardial saturation data will continue to be collected as per Table 1 for a further period of 60 minutes.

Data Analysis

Graphic representation of the change in myocardial oxygen saturation over time will be plotted for each instance. As further detailed herein, the processor 58 receives and processes spectrographic data from the photonic needles 10 to determine oxygen saturation within the myocardium 12.

Specific parameters for each data set will be determined in the following manner:
1. Time from administration of cardioplegia solution until commencement of decline in oxygen saturation (defined as a decrease of more than 5% from baseline).
2. The area under the curve of the plot of change in oxygen saturation over time for each instance will be calculated, starting from the time of cardioplegia solution administration until the second dose of cardioplegia administration (for Sub-Protocol A and C), or for a period of 1 hour after administration of cardioplegia solution (for Sub-Protocol B), or for 1 hour after the second administration of cardioplegia solution (for Sub-Protocol A and C).
3. Assuming a linear decline in oxygen saturation over time (once oxygen saturation begins to decline), the rate of decline will be calculated for each instance according to the following formula:

$$\text{change in saturation/minutes}$$

Where:
change in saturation=the starting myocardial tissue oxygen saturation (immediately after the first administration of cardioplegia solution)−the final myocardial tissue oxygen saturation (immediately prior to administration of the second cardioplegia solution (for Sub-Protocol A and C), or the final saturation at 1 hour (after the second administration of cardioplegia solution for Sub-Protocol A and C, or for Sub-Protocol B)); and Where:
minutes=time from administration of cardioplegia until administration of the second dose of cardioplegia solution (for Sub-Protocol A and C), or from the first administration of cardioplegia solution (for Sub-Protocol B), or the second administration of cardioplegia solution (for Sub-Protocol A and C) until 1 hour has elapsed.

TABLE 1

| Measurement/Time Point | Systemic Arterial Saturation | Systemic BP | Arterial $pO_2$ | Core Temperature | Surface Electrical Activity | Myocardial Temperature | Myocardial Saturation |
|---|---|---|---|---|---|---|---|
| After GA Established | | | | | | | |
| After CPB Cannula Insertion | | | | | | | |
| After CPB Commenced | | | | | | | |
| After Cooling to 25° F. | | | | | | | |
| After Aortic Cross-Clamping and Cardioplegia Administration (Admin # 1) | | | | | | | |
| T + 5 minutes | | | | | | | |
| T + 10 minutes | | | | | | | |
| T + 15 minutes | | | | | | | |
| T + 20 minutes | | | | | | | |
| T + 25 minutes | | | | | | | |
| T + 30 minutes Cardioplegia Administration (Admin # 2) | | | | | | | |
| T + 5 minutes | | | | | | | |
| T + 10 minutes | | | | | | | |
| T + 15 minutes | | | | | | | |
| T + 20 minutes | | | | | | | |
| T + 25 minutes | | | | | | | |
| T + 30 minutes | | | | | | | |
| T + 35 minutes | | | | | | | |
| T + 40 minutes | | | | | | | |
| T + 45 minutes | | | | | | | |
| T + 50 minutes | | | | | | | |
| T + 55 minutes | | | | | | | |
| T + 60 minutes | | | | | | | |

TABLE 1-continued (Sub-Protocol A and C)

| Measurement/ Time Point | Systemic Arterial Saturation | Systemic BP | Arterial pO$_2$ | Core Temperature | Surface Electrical Activity | Myocardial Temperature | Myocardial Saturation |
| --- | --- | --- | --- | --- | --- | --- | --- |
| Cross Clamp Release/ Reperfusion/ Sinus Rhythm | | | | | | | |
| T + 5 minutes | | | | | | | |
| T + 10 minutes | | | | | | | |
| T + 15 minutes | | | | | | | |
| T + 20 minutes | | | | | | | |
| T + 25 minutes | | | | | | | |
| T + 30 minutes | | | | | | | |
| T + 35 minutes | | | | | | | |
| T + 40 minutes | | | | | | | |
| T + 45 minutes | | | | | | | |
| T + 50 minutes | | | | | | | |
| T + 55 minutes | | | | | | | |
| T + 60 minutes | | | | | | | |

TABLE 2

(Sub-Protocol B)

| Measurement/ Time Point | Systemic Arterial Saturation | Systemic BP | Arterial pO$_2$ | Core Temperature | Surface Electrical Activity | Myocardial Temperature | Myocardial Saturation |
| --- | --- | --- | --- | --- | --- | --- | --- |
| After GA Established | | | | | | | |
| After CPB Cannula Insertion | | | | | | | |
| After CPB Commenced | | | | | | | |
| After Aortic Cross-Clamping and Cardioplegia Administration | | | | | | | |
| T + 5 minutes | | | | | | | |
| T + 10 minutes | | | | | | | |
| T + 15 minutes | | | | | | | |
| T + 20 minutes | | | | | | | |
| T + 25 minutes | | | | | | | |
| T + 30 minutes | | | | | | | |
| T + 35 minutes | | | | | | | |
| T + 40 minutes | | | | | | | |
| T + 45 minutes | | | | | | | |
| T + 50 minutes | | | | | | | |
| T + 55 minutes | | | | | | | |
| T + 60 minutes | | | | | | | |
| Cross Clamp Release/ Reperfusion/ Sinus Rhythm | | | | | | | |
| T + 5 minutes | | | | | | | |
| T + 10 minutes | | | | | | | |
| T + 15 minutes | | | | | | | |
| T + 20 minutes | | | | | | | |
| T + 25 minutes | | | | | | | |
| T + 30 minutes | | | | | | | |
| T + 35 minutes | | | | | | | |
| T + 40 minutes | | | | | | | |
| T + 45 minutes | | | | | | | |
| T + 50 minutes | | | | | | | |
| T + 55 minutes | | | | | | | |
| T + 60 minutes | | | | | | | |

Appendix 1a: Cardio-Pulmonary Bypass Circuit Prime Constitution
Plasmalyte A—4 liters
NaHCO3 (50 meq/50 ml)—one 50 mL vials
Osmitrol (20% mannitol)—one 250 mL bag
Heparin (1000 unit/mL)—4 vials
CaCl 10%—1 vial
Appendix 1b: Cardioplegia Solution Constitution
Plasmalyte A—1 liter
KCL (60 meq/60 ml)—two 60 ml vials
NaHCO3 (50 meq/50 ml)—two vials
Blood cardioplegia ratio—4 blood: 1 crystalloid solution
(as much as 6-12 times this volume may be needed for continuous infusions)
Intermittent Cardioplegia Administration:
5 ml/kg/min for 4 minutes
Continuous Cardioplegia Administration:
5 ml/min/min Continuous Infusion Although the invention has been described in detail with reference to certain preferred embodiments, variations and modifications exist within the spirit and scope of the invention as described and defined in the following claims.

The invention claimed is:
1. A method comprising the steps of:
 i. inserting a distal end of a first photonic needle within myocardium;
 ii. emitting light from the distal end of the first photonic needle within the myocardium;
 iii. detecting light reflected from the myocardium;
 iv. processing the reflected light to measure oxygen saturation of the myocardium;
 v. establishing a baseline oxygen saturation level of the myocardium;
 vi. repeating the emitting, detecting and processing steps;
 vii. wherein when the measured oxygen saturation of the myocardium decreases by more than 15% from the baseline oxygen saturation level, then the myocardium is identified as in need of a corrective intervention that would better protect the myocardium in an ischemic environment; and
 viii. wherein providing the corrective intervention includes the step of applying a cardioplegia solution to the myocardium to reduce metabolic activity.
2. The method of claim 1, wherein a decrease in the measured oxygen saturation of the myocardium from the baseline oxygen saturation level during protected cardiac arrest is indicative of ongoing myocardial aerobic and metabolic activity.
3. The method of claim 1, wherein the first photonic needle includes a shaft, a first optic fiber within the shaft for emitting light from the distal end, and a second optic fiber within the shaft for receiving the reflected light.
4. The method of claim 1, wherein the step of providing corrective action further includes the step of applying additional cardioplegia solution.
5. The method of claim 1, wherein the step of providing corrective action further includes the step of altering the composition of the cardioplegia solution.
6. The method of claim 1, further comprising the steps of:
 ix. inserting a distal end of a second photonic needle within the myocardium;
 x. emitting light from the distal end of the second photonic needle within the myocardium;
 xi. detecting light reflected from the myocardium;
 xii. processing the reflected light to measure oxygen saturation of the myocardium; and
 wherein the first photonic needle is positioned within the myocardium at the left ventricle of a heart, and the second photonic needle is positioned within the myocardium at the right ventricle of the heart.
7. The method of claim 1, further comprising the step of placing a myocardial temperature probe adjacent to the first photonic needle to measure temperature of the myocardium.
8. The method of claim 7, further comprising the step of maintaining the measured temperature of the myocardium within 3° C. of a stable temperature by repeated application of reduced temperature saline.
9. The method of claim 7, wherein the step of applying a cardioplegia solution to the myocardium is at a reduced temperature of between 3° C. and 5° C.
10. The method of claim 9, wherein the step of applying a cardioplegia solution to the myocardium includes infusing the cardioplegia solution ante-grade into the aortic root of a heart.
11. The method of claim 7, further comprising the step of applying electrodes to the myocardium to produce an electrocardiogram.
12. A method of measuring oxygen saturation in the myocardium, the method comprising the steps of:
 i. inserting a first photonic needle within the myocardium, wherein the first photonic needle includes a shaft, a first optic fiber extending within the shaft and coupled to a light source, and a second optic fiber extending within the shaft and coupled to a light detector;
 ii. emitting light from the first optic fiber;
 iii. collecting light with the second optic fiber;
 iv. obtaining spectroscopic data from light delivered and collected from the myocardium via the photonic needle;
 v. processing the spectroscopic data to measure oxygen saturation of the myocardium;
 vi. determining active myocardial metabolic activity based upon a change in measured oxygen saturation of the myocardium; and
 vii. wherein when the change in measured oxygen saturation of the myocardium is greater than 15%, then the myocardium is identified as in need of a corrective intervention that would better protect the myocardium in an ischemic environment; and
 viii. wherein providing the corrective intervention includes the step of applying a cardioplegia solution to the myocardium to reduce metabolic activity.
13. The method of claim 12, further comprising the steps of:
 ix. inserting a distal end of a second photonic needle within the myocardium;
 x. emitting light from the distal end of the second photonic needle within the myocardium;
 xi. detecting light reflected from the myocardium;
 xii. processing the reflected light to measure oxygen saturation of the myocardium; and
 wherein the first photonic needle is positioned within the myocardium at the left ventricle of a heart, and the second photonic needle is positioned within the myocardium at the right ventricle of the heart.
14. The method of claim 12, further comprising the step of placing a myocardial temperature probe adjacent to the first photonic needle to measure temperature of the myocardium.
15. The method of claim 14, further comprising the step of maintaining the measured temperature of the myocardium within 3° C. of a stable temperature by repeated application of reduced temperature saline.

16. The method of claim 14, wherein the step of applying a cardioplegia solution to the myocardium is at a reduced temperature of between 3° C. and 5° C.

17. The method of claim 16, wherein the step of applying a cardioplegia solution to the myocardium includes infusing the cardioplegia solution ante-grade into the aortic root of a heart.

18. The method of claim 14, further comprising the step of applying electrodes to the myocardium to produce an electrocardiogram.

* * * * *